(12) United States Patent
Park et al.

(10) Patent No.: US 9,969,358 B2
(45) Date of Patent: May 15, 2018

(54) MULTIFOCAL RAIN SENSOR

(71) Applicants: Hyundai Motor Company, Seoul (KR); Kia Motors Corporation, Seoul (KR)

(72) Inventors: Jong Min Park, Seoul (KR); Nak Kyoung Kong, Gyeonggi-do (KR); Keon Soo Jin, Ulsan (KR); Ki Hong Lee, Seoul (KR); Jin Sang Lee, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 87 days.

(21) Appl. No.: 15/269,486

(22) Filed: Sep. 19, 2016

(65) Prior Publication Data
US 2017/0291581 A1    Oct. 12, 2017

(30) Foreign Application Priority Data

Apr. 7, 2016 (KR) .......................... 10-2016-0042608

(51) Int. Cl.
*B60S 1/08* (2006.01)
*G01N 21/3577* (2014.01)
*G01N 21/55* (2014.01)
*G02B 17/06* (2006.01)

(52) U.S. Cl.
CPC ........ *B60S 1/0833* (2013.01); *G01N 21/3577* (2013.01); *G01N 21/55* (2013.01); *G02B 17/0621* (2013.01); *G01N 2201/0621* (2013.01)

(58) Field of Classification Search
USPC ....................................................... 250/353
See application file for complete search history.

(56) References Cited

U.S. PATENT DOCUMENTS 5,661,303 A * 8/1997 Teder ..................... G01N 21/43
250/227.25

FOREIGN PATENT DOCUMENTS

| JP | 1998-300861 A | 11/1998 |
| JP | 1999-509932 A | 8/1999 |
| JP | 2000-193586 A | 7/2000 |
| JP | 2014-211358 A | 11/2014 |
| KR | 10-1983-0008132 A | 11/1983 |
| KR | 2009-0111770 A | 10/2009 |
| KR | 2015-0137897 A | 12/2015 |

* cited by examiner

*Primary Examiner* — Edwin Gunberg
(74) *Attorney, Agent, or Firm* — Mintz Levin Cohn Ferris Glovsky and Popeo, P.C.; Peter F. Corless

(57) ABSTRACT

A multifocal rain sensor includes: at least one light emitting unit configured to output light; a first reflective plate corresponding to the at least one light emitting unit and disposed at a position spaced apart from the at least one light emitting unit by a predetermined distance; a glass part reflecting light after the light is reflected by the first reflective plate and forming a sensing region; a second reflective plate re-reflecting the light reflected by the glass part; and a light receiving unit configured to receive the light reflected by the second reflective plate. The second reflective plate includes a multifocal reflective plate having a plurality of focuses based on a vertical height of incident light that varies according to a change in thickness of the glass part.

13 Claims, 8 Drawing Sheets

[ 4T GLASS RAY TRACING ]

[ 5T GLASS RAY TRACING ]

[ SYSTEM IN WHICH MULTIFOCAL STEPPED REFLECTOR IS APPLIED TO LIGHT RECEIVING UNIT AND LONG/MIDDLE/SHORT FOCUSES ARE USED ]

< EMBODIMENT2 >

MULTIFOCAL RAIN SENSOR

CROSS-REFERENCE TO RELATED APPLICATION

This application claims under 35 U.S.C. § 119(a) the benefit of and priority to Korean Patent Application No. 10-2016-0042608 filed on Apr. 7, 2016, the entire contents of which are incorporated herein by reference as if fully set forth herein.

BACKGROUND

(a) Technical Field

The present disclosure relates generally to a multifocal rain sensor and, more particularly, to a multifocal rain sensor which is configured such that a single rain sensor configuration can be used for various glass parts having different focuses.

(b) Background Art

A rain sensor, also called a rain detector or a rain detecting sensor, is a device which can be equipped in a vehicle to automatically sense characteristics, such as the intensity, the amount, etc., of rainwater and control operation of a wiper (e.g., the speed, the operating time, etc.) even when a driver does not manually control the wiper. Notably, if the driver attempts to control the operation or speed of the wiper while driving, the risk of an accident may increase, or the driver may experience inconvenience from having to turn away his/her eyes or have unnecessary motion while driving. The rain sensor was created to overcome the foregoing problems.

In detail, the rain sensor is designed in such a way that, when rainwater falls onto a windshield of a vehicle, the rain sensor installed on a rear surface of the windshield senses the amount and speed of rainwater using infrared rays and controls the wiper to increase or reduce its speed depending on the amount and speed of sensed rainwater. It is important to accurately measure the amount of rainwater to effectively control the speed of the wiper of the vehicle. To more accurately measure the amount of rainwater, light emitted from a light emitting unit must be efficiently collected.

However, since the thickness of glass parts varies depending on the kind of vehicles, separate rain sensors appropriate for the respective glass parts must be provided, or changes in design of the existing rain sensors are required to be adapted for various kinds of glass parts. Furthermore, due to limitations in space, material and dioptrics, it can be difficult to collect reflected light which is incident on a wide region at a short distance. Due to this, there is a problem in that the size of the sensor must be increased to improve the efficiency of the sensor.

Conventionally, a rain sensor measures the amount of rainwater falling onto a glass part in such a way that light emitted from a lighting emitting unit is directly collected to a light receiving unit, demonstrated in FIG. 1. As shown in FIG. 1, the conventional rain sensor 30 includes a light emitting unit 11 which emits light, a reflective plate 12 which reflects light emitted from the light emitting unit 11, a glass part 20 which re-reflects light reflected by the reflective plate 12 and forms a sensing region, and a light receiving unit 13 which receives light reflected by the glass part 20.

However, there is no separate configuration for collecting all reflected light which is horizontally incident. Therefore, the rain sensor 30 is problematic in that light collection efficiency of the light receiving unit 13 is reduced. Moreover, because the rain sensor is configured for only one kind of glass part, separate reflective plates having different focuses depending on the thickness of different kinds of glass parts must be provided. Thus, in a case where a rain sensor having multiple focuses corresponding to the thicknesses of different kinds of glass parts is required, the conventional rain sensor 30 cannot be employed.

The above information disclosed in this Background section is only for enhancement of understanding of the background of the disclosure, and therefore it may contain information that does not form the related art that is already known in this country to a person of ordinary skill in the art.

SUMMARY OF THE DISCLOSURE

The present disclosure has been made in an effort to solve the above-described problems associated with the related art.

An object of the present disclosure is to provide a multifocal rain sensor which includes a second reflective plate having multiple focuses and thus can be applied to all vehicles in which different focuses are required depending on the thicknesses of glass parts therein.

Another object of the present disclosure is to provide a rain sensor which employs the multifocal second reflective plate and thus is able to receive all incident light having different phases depending on the position.

Still another object of the present disclosure is to provide a rain sensor which is configured such that light that is reflected by the glass part and is incident on the second reflective plate disposed adjacent to the light receiving unit, is reflected by the second reflective plate and thus collected into the light receiving unit, whereby the light collection efficiency of the rain sensor can be enhanced.

According to embodiments of the present disclosure, a multifocal rain sensor includes: at least one light emitting unit configured to output light; a first reflective plate corresponding to the at least one light emitting unit and disposed at a position spaced apart from the at least one light emitting unit by a predetermined distance; a glass part reflecting light after the light is reflected by the first reflective plate and forming a sensing region; a second reflective plate re-reflecting the light reflected by the glass part; and a light receiving unit configured to receive the light reflected by the second reflective plate. The second reflective plate includes a multifocal reflective plate having a plurality of focuses based on a vertical height of incident light that varies according to a change in thickness of the glass part.

The second reflective plate may have steps having a stepped shape, and the steps of the second reflective plate having the stepped shape may be configured such that reflected light having different phases according to the thickness of the glass part is received by the light receiving unit.

The second reflective plate may be configured with a multifocal parabolic reflective plate.

A focus of the second reflective plate may be larger than a focus of the first reflective plate.

The plurality of focuses of the second reflective plate may be determined by $x^2=4 \times f \times y$, where x denotes a distance between the second reflective plate and the light receiving unit, y denotes a height of the second reflective plate, and f denotes a focal distance of the second reflective plate.

The second reflective plate may be configured with a parabolic reflective plate having a predetermined curvature with respect to a vertical direction causing different focuses, and having a spherical shape with respect to a horizontal direction.

The at least one light emitting unit may be configured with an infrared light-emitting diode (LED).

The thickness of the glass part may range from approximately 4 mm to approximately 6 mm.

The multifocal rain sensor may further include a parallel unit disposed on an inner surface of the glass part. The parallel unit may make light reflected by at least one of the first reflective plate and the second reflective plate form parallel light.

The parallel unit may be configured with a serrated lens.

The parallel unit may be provided on the sensing region of the glass part and configured to have a bilateral symmetry structure.

The at least one light emitting unit may be configured with two or more light emitting units configured to control light to be received by the light receiving unit through time separation.

Furthermore, in accordance with embodiments of the present disclosure, a vehicle includes: a multifocal rain sensor; and a control unit having a memory to store program instructions and a processor to execute the stored program instructions and configured to control an operation of one or more wipers equipped in the vehicle according to information sensed by the multifocal rain sensor, wherein the multifocal rain sensor includes: at least one light emitting unit configured to output light; a first reflective plate corresponding to the at least one light emitting unit and disposed at a position spaced apart from the at least one light emitting unit by a predetermined distance; a glass part reflecting light after the light is reflected by the first reflective plate and forming a sensing region; a second reflective plate re-reflecting the light reflected by the glass part; and a light receiving unit configured to receive the light reflected by the second reflective plate, wherein the second reflective plate includes a multifocal reflective plate having a plurality of focuses based on a vertical height of incident light that varies according to a change in thickness of the glass part.

Other aspects and preferred embodiments of the disclosure are discussed infra.

BRIEF DESCRIPTION OF THE DRAWINGS

The above and other features of the present disclosure will now be described in detail with reference to embodiments thereof illustrated the accompanying drawings which are given hereinbelow by way of illustration only, and thus are not limitative of the present disclosure, and wherein.

Figure 1:
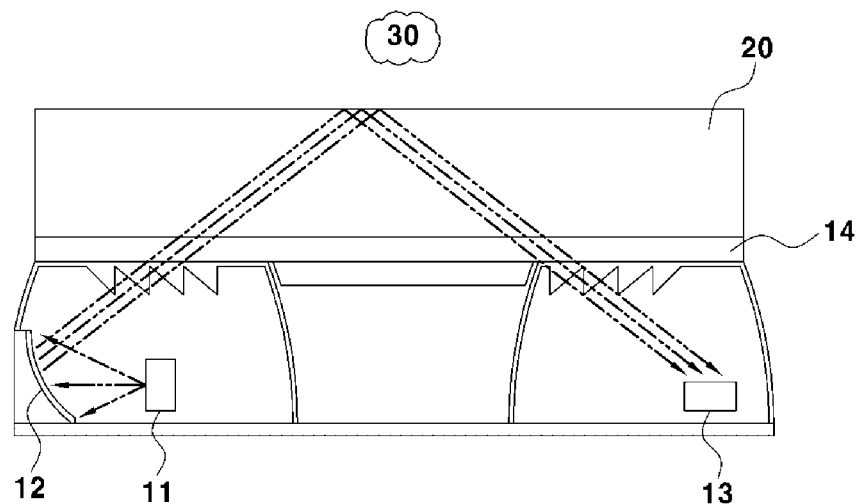
FIG. 1 illustrates a conventional rain sensor in which reflected light is directly emitted to a light receiving unit.

It should be understood that the appended drawings are not necessarily to scale, presenting a somewhat simplified representation of various preferred features illustrative of the basic principles of the disclosure. The specific design features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawing.

DETAILED DESCRIPTION OF THE EMBODIMENTS

Hereinafter reference will now be made in detail to various embodiments of the present disclosure, examples of which are illustrated in the accompanying drawings and described below. While the disclosure will be described in conjunction with exemplary embodiments, it will be understood that present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. Further, in the following detailed description, names of constituents, which are in the same relationship, are divided into "the first," "the second," etc., but the present disclosure is not necessarily limited to the order in the following description. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one control unit (not shown). The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Furthermore, the control unit of the present disclosure may be embodied as non-transitory computer readable media containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed throughout a computer network so that the program instructions are stored and executed in a distributed fashion, e.g., by a telematics server or a Controller Area Network (CAN).

Referring now to the presently disclosed embodiments, the present disclosure relates to a total reflection rain sensor using a mirror which is attached to a glass window of a vehicle and senses raindrops falling onto the vehicle glass window and outputs a signal for controlling the speed and period of a wiper of the vehicle depending on the amount of sensed raindrops and the period of falling of raindrops. Further, the rain sensor may be attached not only to a front windshield of the vehicle but also to any glass window with a wiper among the glass windows of the vehicle (e.g., the glass of the rear window).

Figure 2:
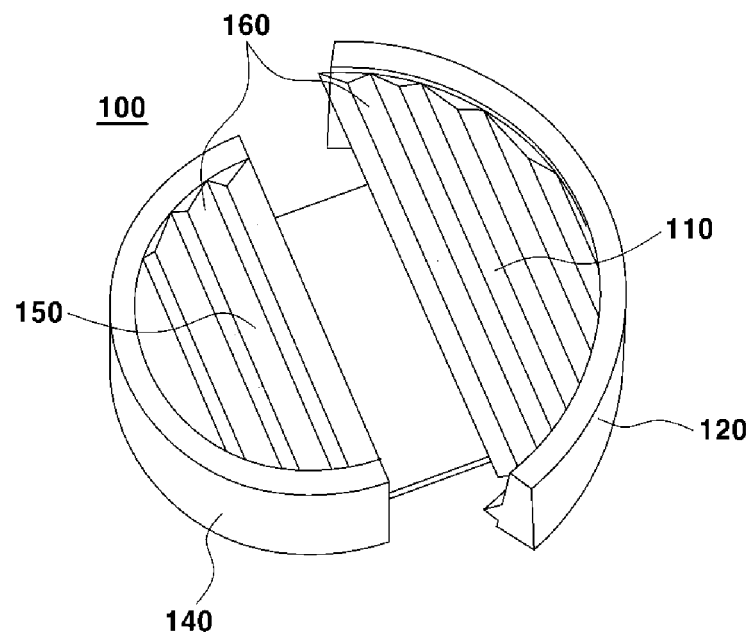
FIG. 2 is a perspective view illustrating a multifocal rain sensor including a curved multifocal second reflective plate, according to embodiments of the present disclosure.

FIG. 2 is a perspective view illustrating a multifocal rain sensor 100, according to embodiments of the present disclosure.

The multifocal rain sensor 100 includes at least one light emitting unit 110 which is disposed in a rain sensor housing. The light emitting unit 110 is located on a surface of the housing that is opposite to another surface thereof contacting a glass part 130 of the vehicle, and is oriented to emit light in a horizontal direction of the housing. The light emitting unit 110 may be configured with an infrared LED which emits infrared light. Furthermore, the light emitting unit is configured to face a first reflective plate 120 on the same horizontal plane and is disposed such that light emitted from the light emitting unit 110 is reflected by the first reflective plate 120.

The multifocal rain sensor 100 further includes a light receiving unit 150 which is a configuration corresponding to the light emitting unit 110. The light receiving unit 150 is configured with a photodiode which receives light emitted from the light emitting unit 110. The photodiode is coupled to a PCB 200 disposed in the housing and configured to receive a measured value of light received depending on the amount of rainwater. The light receiving unit 150 is configured to face a second reflective plate 140. Light that is emitted from the light emitting unit 110 and reflected by the first reflective plate 120 is reflected by the second reflective plate 140 and collected into the light receiving unit 150. That is, the second reflective plate 140 has a predetermined curvature to collect reflected light that is vertically incident thereon. Furthermore, the second reflective plate 140 may also include a configuration having a predetermined curvature or a curved surface shape to collect reflected light that is horizontally incident thereon. As described above, the second reflective plate 140 configured to collect light emitted from the light emitting unit 110 and reflected by the reflective plates has different focuses depending on the vertical height. The focuses may be set depending on reflected light which has different phases depending on the thickness of the glass part 130.

In one example, the light emitting unit 110 of the present disclosure may comprise two or more light emitting units 110. In this case, light emitted from the plurality of light emitting units 110 is received into the light receiving unit 150. The light emitting units 110 may separate the time for which light is emitted, through time separation. All light emitted in this way can be received by the light receiving unit 150.

Furthermore, the embodiments of the present disclosure are configured to include the single receiving unit 150. Light that is emitted from the two or more light emitting units 110 in the time separation manner is sequentially received into the single light receiving unit 150. As such, light emitted from the plurality of light emitting units 110 can be received by the configuration having the single light receiving unit 150.

Figure 3:
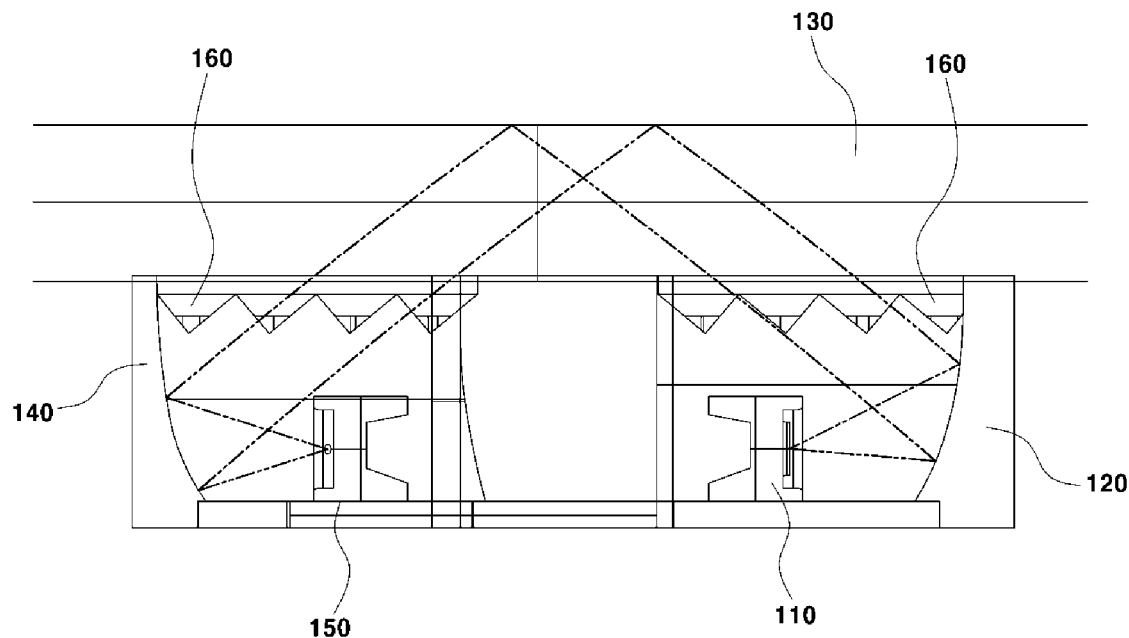
FIG. 3 is a side sectional view illustrating the multifocal rain sensor including the curved multifocal second reflective plate, according to embodiments of the present disclosure.

FIG. 3 is a side sectional view illustrating the multifocal rain sensor 100, according to embodiments of the present disclosure.

The light emitting unit 110 disposed in the rain sensor housing is configured to horizontally emit light. The emitted light is emitted to the first reflective plate 120 spaced apart from the light emitting unit 110 by a predetermined distance. The emitted light is reflected by the first reflective plate 120 and then is incident on the outside of the glass part 130 of the vehicle. Furthermore, a parallel unit 160 may be provided at a position before light is incident on the outside of the glass part 130 of the vehicle. Reflected light may pass through the parallel unit 160 and thus have the form of parallel light. However, reflected light that has passed through the parallel unit 160 may form different type optical paths depending on the shape of the rain sensor and a sensing area. More preferably, the parallel unit 160 may be symmetrically provided based on the center of a sensing region of the glass part and configured to maintain or change the path of light which passes through the parallel unit 160.

Furthermore, reflected light is totally reflected at the outside of the glass part 130 of the vehicle. Reflected light re-reflected by the glass part 130 is emitted to the second reflective plate 140. The second reflective plate 140 may be configured with a multifocal parabolic mirror having different focuses depending on the vertical height. The second reflective plate 140 having the above-mentioned configuration reflects light emitted thereto and thus functions to collect reflected light that is incident on the second reflective plate 140, into the light receiving unit 150 that faces the second reflective plate 140. For instance, the second reflective plate 140 has a focus value larger than that of the first reflective plate 120 so that the area of a region in which the second reflective plate 140 can collect incident light is greater than that of the first reflective plate 120.

The second reflective plate 140 having a multifocal structure may have a large diameter so that all reflected light having different phases depending on the thickness of the glass part 130 can be reflected by the second reflective plate 140. In addition, the second reflective plate 140 has different focuses depending on the height such that reflected light having different phases is re-reflected and received into the light receiving unit 150. More preferably, the second reflective plate 140 of the present disclosure may have a curved (e.g., parabolic) shape to have different focuses depending on the vertical height. Given this, as the thickness of the glass part is increased, focal length of reflected light is increased, and the reflected light is emitted to an upper portion of the second reflective plate 140 in a vertical direction. Furthermore, the second reflective plate 140 is configured to have a spherical surface shape with respect to the horizontal direction such that reflected light emitted in the horizontal direction is collected into the light receiving unit 150.

Figure 4:
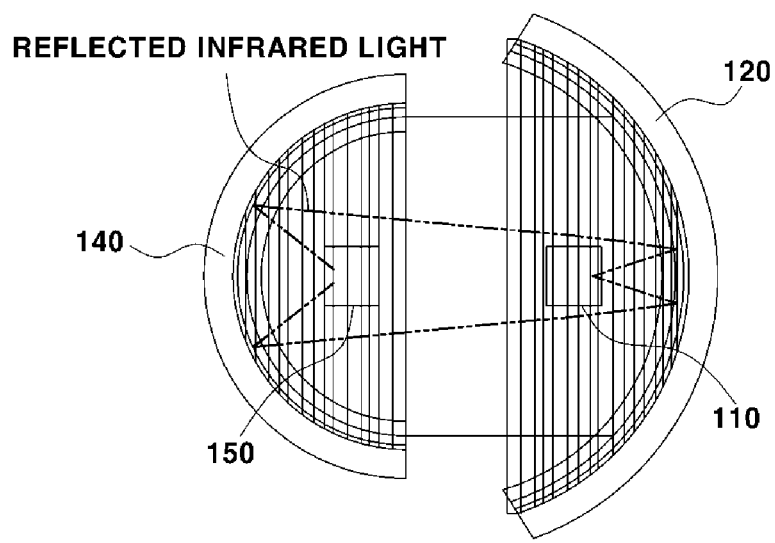
FIG. 4 illustrates a path of light in the multifocal rain sensor including the curved multifocal second reflective plate, according to embodiments of the present disclosure.

FIG. 4 is a front view of the multifocal rain sensor 100 including the second reflective plate 140 configured with a multifocal parabolic mirror, according to embodiments of the present disclosure.

In the rain sensor configured with the infrared LED light emitting unit 110, light emitted from the light emitting unit 110 is reflected by the first reflective plate 120, passes through the serrated parallel unit 160, and then is incident on the glass part 130. Light that is incident on the outside of the glass part 130 is totally reflected at the outside of the glass part 130 and thus is incident on the second reflective plate 140. The second reflective plate 140 is formed of a large-diameter long-focus reflective plate. Furthermore, the second reflective plate 140 is configured such that it has a predetermined curvature with respect to the vertical direction and thus is able to collect reflected light which is emitted thereto in the vertical direction, and it has a spherical surface shape with respect to the horizontal direction and thus is able to collect reflected light which is emitted thereto in the horizontal direction. Light re-reflected by the second reflective plate 140 is collected into the light receiving unit 150.

Figure 5:
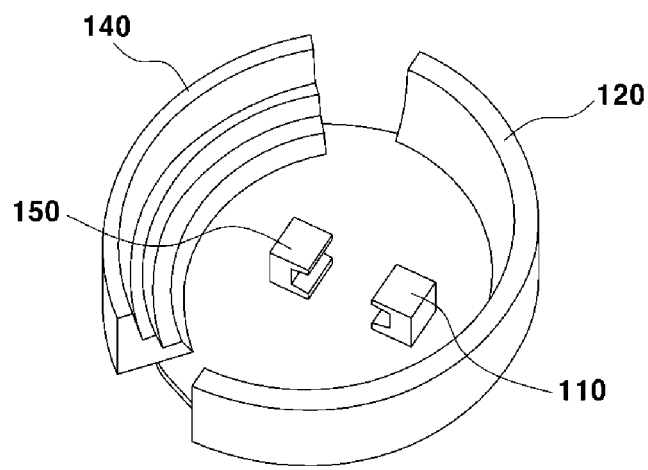
FIG. 5 is a perspective view illustrating a multifocal rain sensor including a step-shaped multifocal second reflective plate, according to embodiments of the present disclosure.

FIG. 5 is a perspective view of a multifocal rain sensor 100 including a second reflective plate 140 configured with a mirror having a stepped shape, according to embodiments of the present disclosure.

FIG. 5 illustrates the same configuration as that described with reference to FIG. 2, but the second reflective plate 140 according to this embodiment has a stepped structure having multiple focuses. For instance, the second reflective plate 140 having a three-stepped structure includes, on the uppermost step thereof, a reflective plate having a long focus. As the stepped portions are close to the bottom of the housing, the focal lengths of reflective plates forming the second reflective plate 140 are reduced. Furthermore, each of the reflective plates forming the respective stepped portions constituting the second reflective plate 140 may have a curved shape, and each of the stepped portions defining the steps of the second reflective plate 140 may be configured to have a predetermined inclination.

Figure 6:
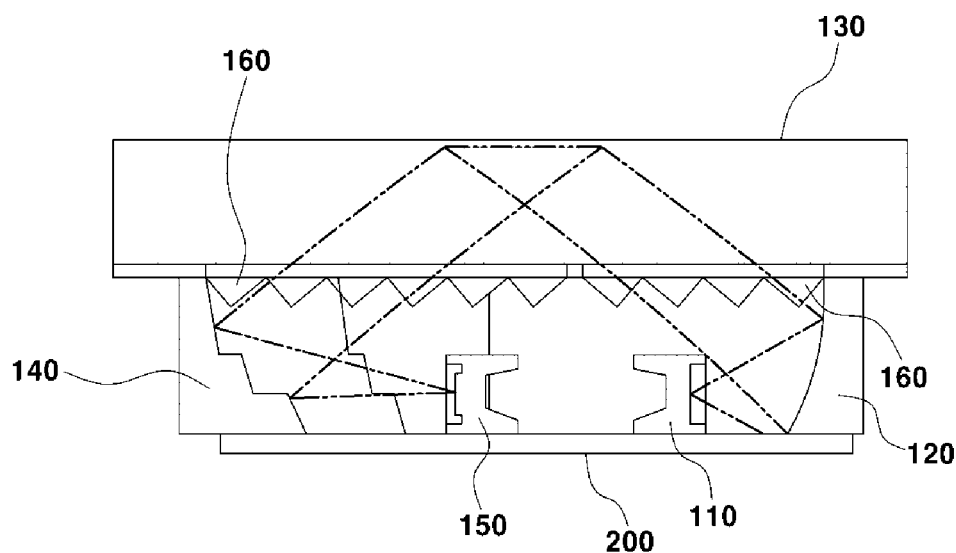
FIG. 6 is a side sectional view illustrating the multifocal rain sensor including the step-shaped multifocal second reflective plate, according to embodiments of the present disclosure.

FIG. 6 is a side sectional view of the multifocal rain sensor 100 including the second reflective plate 140 configured with the mirror having a stepped shape, according to embodiments of the present disclosure.

A light emitting unit 110 disposed in the rain sensor housing is configured to horizontally emit light. The emitted light is emitted to a first reflective plate 120 spaced apart from the light emitting unit 110 by a predetermined distance. The emitted light is reflected by the first reflective plate 120 and then is incident on the outside of the glass part 130 of the vehicle. Furthermore, a parallel unit 160 may be provided at a position before light is incident on the outside of the glass part 130 of the vehicle. Reflected light may pass through the parallel unit 160 and thus have the form of parallel light. However, reflected light that has passed through the parallel unit 160 may form different type optical paths depending on the shape and sensing area of the rain sensor.

Furthermore, reflected light is totally reflected at the outside of the glass part 130 of the vehicle. Reflected light re-reflected by the glass part 130 is emitted to the second reflective plate 140. The second reflective plate 140 may be configured with a step-shaped mirror having different focuses depending on the vertical height. More preferably, the second reflective plate 140 is configured with a plurality of stepped portions, each of which has a predetermined curvature with respect to the vertical direction and thus is able to collect reflected light which is emitted thereto in the vertical direction, and each of which has a spherical surface shape with respect to the horizontal direction and thus is able to collect reflected light which is emitted thereto in the horizontal direction.

The second reflective plate 140 having the above-mentioned configuration collects light into a light receiving unit 150 that faces the second reflective plate 140.

For instance, the second reflective plate 140 is configured to have a focus value larger than that of the first reflective plate 120 so that the area of a region in which the second reflective plate 140 can collect incident light is greater then that of the first reflective plate 120.

As such, in the second reflective plate 140 having a multifocal structure, the respective stepped portions of the second reflective plate 140 have different focuses such that, when reflected light having different phases depending on the thickness of the glass part 130 is incident on the second reflective plate 140, the reflected light having different phases is re-reflected by the respective stepped portions of the second reflective plate 140 and collected into the light receiving unit 150.

That is, in the case of the second reflective plate 140 configured with a three-stepped mirror, when the amount of rainwater is measured on a vehicle having a glass part 130 of 6 mm, reflected light incident on the uppermost stepped portion of the second reflective plate 140 is collected into the light receiving unit 150. Compared to this, in the case where the amount of rainwater is measured on a vehicle having a glass part 130 of 5 mm, reflected light is collected into the light receiving unit 150 via the reflective plate disposed on the second stepped portion of the second reflective plate 140. In the case where the amount of rainwater is measured on a vehicle having a glass part 130 of 4 mm, light is collected into the light receiving unit 150 via the reflective plate disposed on the lowermost stepped portion of the second reflective plate 140.

Figure 7A:
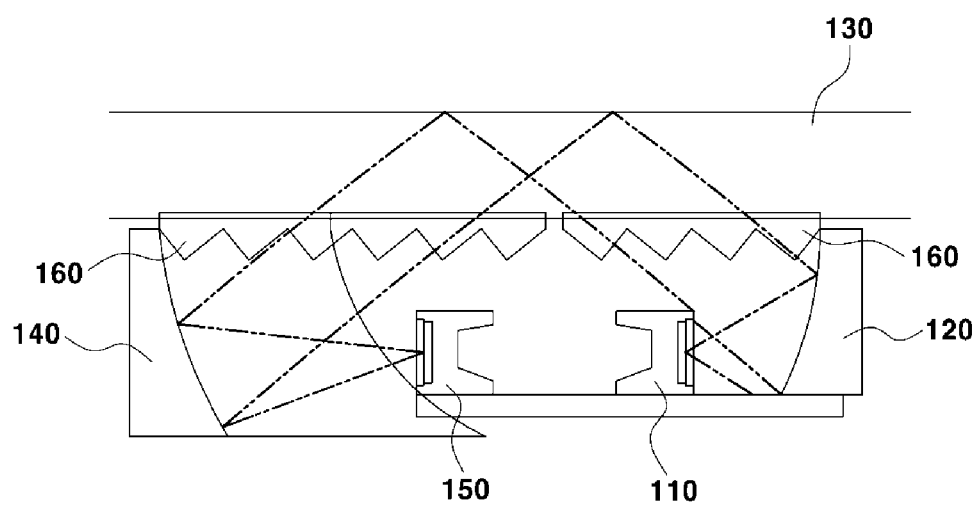
FIG. 7a illustrates a path of light in a multifocal rain sensor including a curved multifocal second reflective plate, in the case of a glass part having a thickness of 4 mm, according to embodiments of the present disclosure.

FIG. 7a is a side view showing the path of light in the rain sensor when the glass part 130 has a thickness of 4 mm, according to embodiments of the present disclosure.

Here, the second reflective plate 140 is configured with a parabolic mirror having three focuses with respect to the horizontal direction and configured such that the focal length of the second reflective plate 140 is increased from the lowermost end thereof to the uppermost end.

Therefore, light of the rain sensor for measuring rainwater disposed on the outer surface of the glass part 130 is emitted from the light emitting unit 110 and reflected by the first reflective plate 120. The light reflected by the first reflective plate 120 is totally reflected at the outside of the glass part 130 of the vehicle, and the reflected light that is re-reflected by the glass part 130 is emitted to the second reflective plate 140. Particularly, the reflected light that is incident on the second reflective plate 140 is incident on the lowermost portion of the second reflective plate 140 in a vertical direction, in other words, is collected into the light receiving unit 150 through the region of the second reflective plate 140 that has the shortest focal length.

Figure 7B:
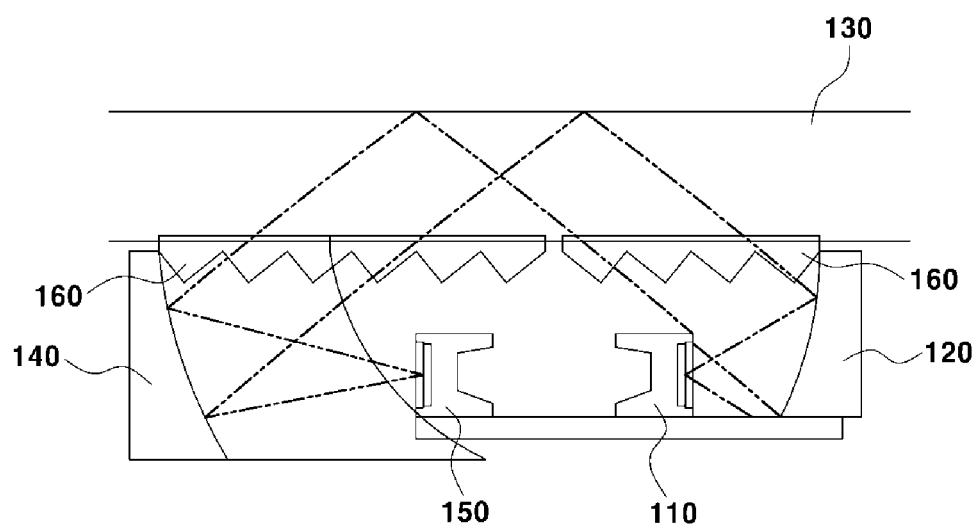
FIG. 7b illustrates a path of light in a multifocal rain sensor including a curved multifocal second reflective plate, in the case of a glass part having a thickness of 5 mm, according to embodiments of the present disclosure.

FIG. 7b is a side view showing the path of light in the rain sensor when the glass part 130 has a thickness of 5 mm, according to embodiments of the present disclosure.

In the same manner as the case of FIG. 7a, the second reflective plate 140 shown in FIG. 7b is configured with a parabolic mirror having three focuses with respect to the horizontal direction and configured such that the focal length of the second reflective plate 140 is increased from the lowermost end thereof to the uppermost end.

Light of the rain sensor for measuring the amount of rainwater is emitted from the light emitting unit 110 and reflected by the first reflective plate 120. The light reflected by the first reflective plate 120 is totally reflected at the outside of the glass part 130 of the vehicle, and the reflected light that is re-reflected by the glass part 130 is emitted to the second reflective plate 140. Particularly, the reflected light that is incident on the second reflective plate 140 is incident on an intermediate portion of the second reflective plate 140 with respect to the vertical direction, in other words, is collected into the light receiving unit 150 through an intermediate region of the second reflective plate 140 that has a middle focal length.

Figure 7C:
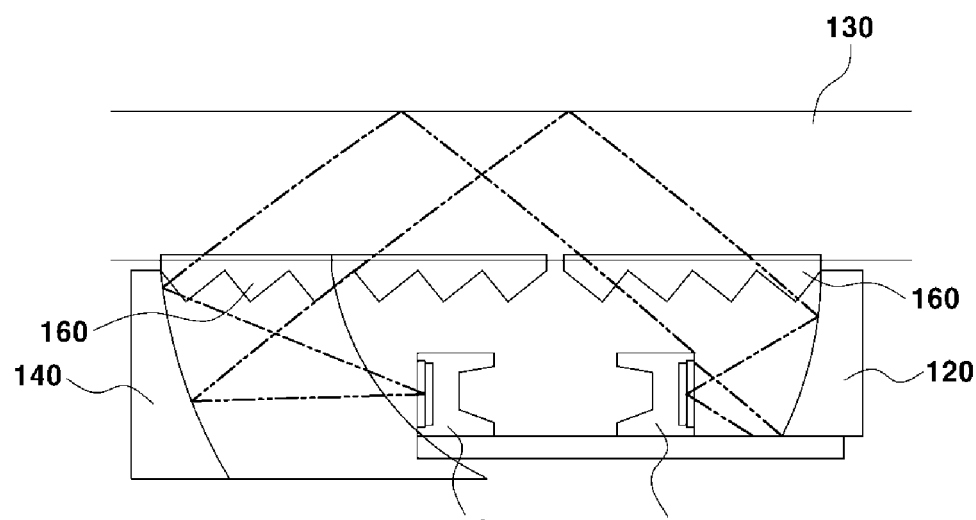
FIG. 7c illustrates a path of light in a multifocal rain sensor including a curved multifocal second reflective plate, in the case of a glass part having a thickness of 6 mm, according to embodiments of the present disclosure.

FIG. 7c is a side view showing the path of light in the rain sensor when the glass part 130 has a thickness of 6 mm, according to embodiments of the present disclosure.

In the same manner as the case of FIG. 7a, the second reflective plate 140 is configured with a step-shaped mirror having three focuses with respect to the horizontal direction and configured such that the focal length of the second reflective plate 140 is increased from the lowermost end thereof to the uppermost end.

Light of the rain sensor for measuring the amount of rainwater is emitted from the light emitting unit 110 and reflected by the first reflective plate 120. The light reflected by the first reflective plate 120 is totally reflected at the outside of the glass part 130 of the vehicle, and the reflected light that is re-reflected by the glass part 130 is emitted to the second reflective plate 140. Particularly, the reflected light that is incident on the second reflective plate 140 is incident on the uppermost portion of the second reflective plate 140 in a vertical direction, in other words, is collected into the light receiving unit 150 through the uppermost region of the second reflective plate 140 that has the longest focal length.

As illustrated in FIGS. 7a to 7c, a difference in phase of reflected light is caused depending on the thickness of the glass part 130. In the case where total reflection is implemented through the glass part 130 having a relatively small thickness, the total reflection is implemented on a region of the glass part 130 that is relatively close to the light emitting part 110, so that reflected light is incident on the lowermost region of the second reflective plate 140. As the thickness of the glass part 130 is increased, the total reflection is implemented on a region of the glass part 130 distant from the light emitting part 110, that is, reflected light is incident on an upper portion of the second reflective plate 140.

Therefore, as the thickness of the glass part 130 is increased, the position at which total reflection is implemented on the glass part 130 is moved to a region close to the light receiving unit 150. In the case where reflected light is totally reflected on a region close to the light receiving unit 150, the reflected light is emitted to the upper portion of the second reflective plate 140 in a vertical direction.

Comparative Example 1

A conventional rain sensor may include a light emitting unit 11, a parallel unit, a light receiving unit 13 and a reflective plate 12. Light receiving performance depending on the thickness of the glass part 20 was measured using the rain sensor of the conventional art that does not include the second reflective plate 140.

Figure 8A:
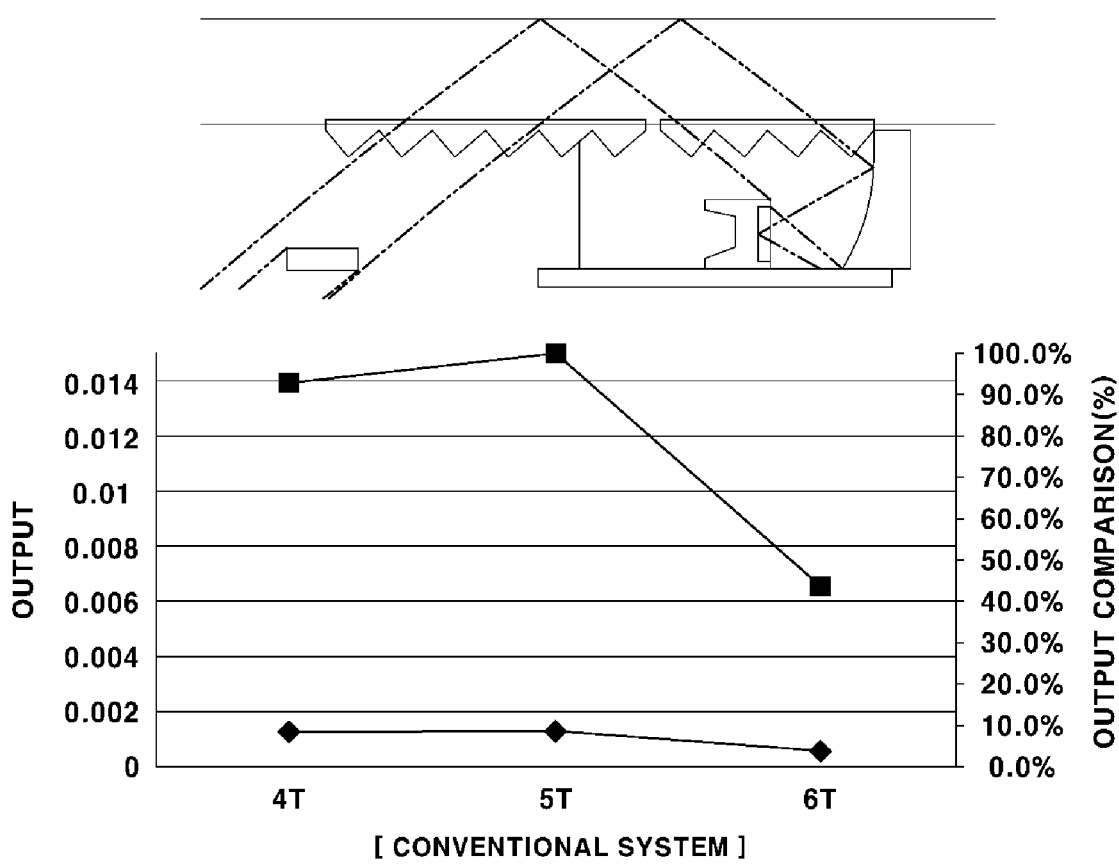
FIG. 8a shows the output of a conventional light receiving unit according to the thickness of a glass part, as a comparative example.
Figure 8B:
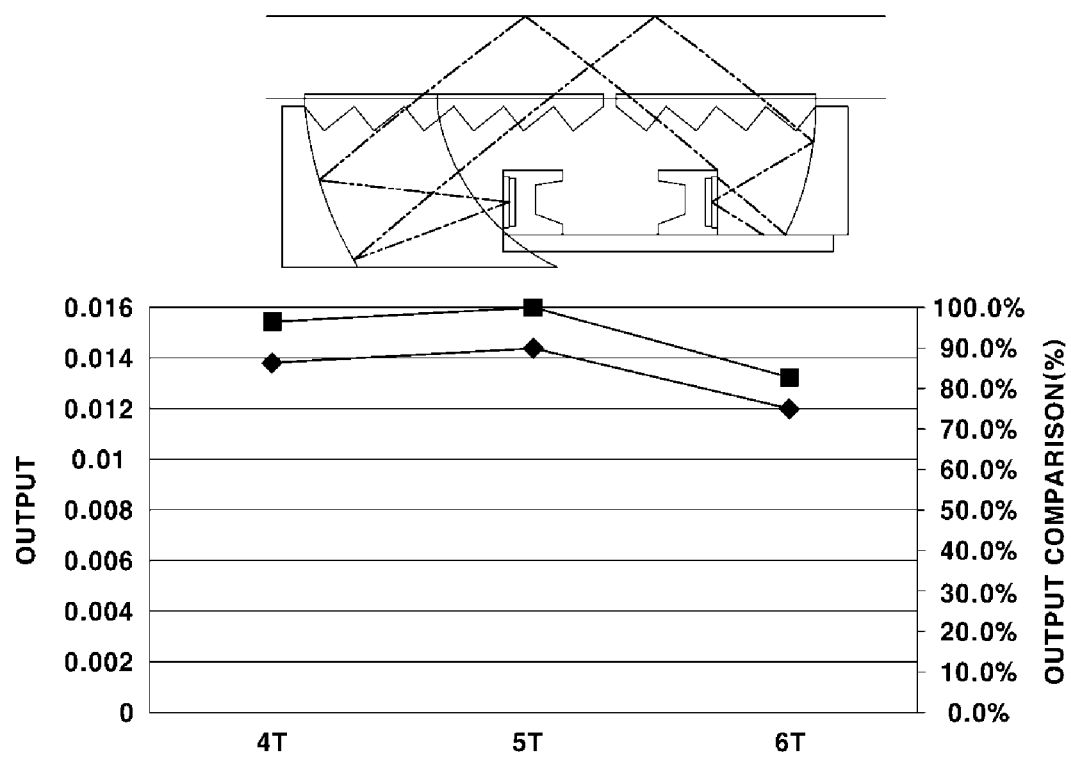
FIG. 8b shows the output of the light receiving unit of the rain sensor including the curved multifocal second reflective plate according to the thickness of a glass part, according to embodiments of the present disclosure.
Figure 8C:
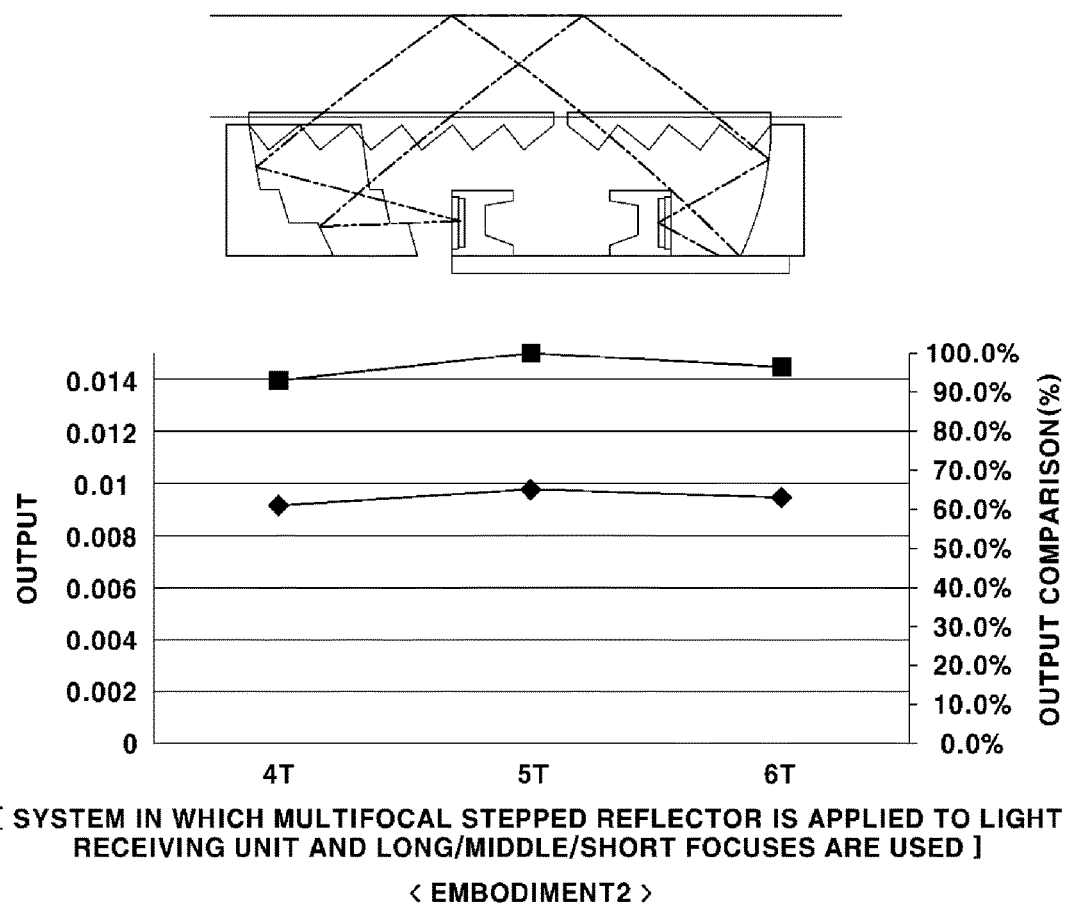
FIG. 8c shows the output of the light receiving unit of the rain sensor including the step-shaped multifocal second reflective plate according to the thickness of a glass part, according to embodiments of the present disclosure.

As shown in FIG. 8a, in the case where the thickness of the glass part 20 is 4 mm, the output was 0.01 W, and the light receiving unit 13 receives 90% of the output value of the light emitting unit 11. Furthermore, in the case where the thickness of the glass part 20 is 5 mm, the light receiving unit 13 receives 95% of the output value of the light emitting unit 11. This indicates that the measurement efficiency of the rain sensor is comparatively high.

However, in the case where the thickness of the glass part 20 is 6 mm, the output measured on the light receiving unit 13 was 0.006 W which is half or less of the output value of the case of the glass part 20 having a thickness 4 mm or 5 mm. The output ratio of the light receiving unit 13 to the output of the light emitting unit 11 was about 40%.

Accordingly, in the case of a conventional rain sensor attached to the glass part having a thickness of 6 mm or more, the output value of light received to the light receiving unit 13 is markedly reduced. Therefore, it is difficult to obtain an accurate measurement value.

Embodiment 1

In Embodiment 1 of the present disclosure, there is provided a multifocal rain sensor 100 including a light emitting unit 110 which emits light, a first reflective plate 120 which reflects light emitted from the light emitting unit 110, a glass part 130, a parallel unit 160 which is attached to an inner surface of the glass part 130, a second reflective plate 140 which is configured with a multifocal parabolic mirror, and a light receiving unit 150. Moreover, the second reflective plate 140 has a long focus and a large diameter. The output of the rain sensor to which the second reflective plate 140 was applied was measured.

As a result of measuring the output of light collected into the light receiving unit 150 through the rain sensor according to Embodiment 1, in the case where the thickness of the glass part 130 is 4 mm, the output value was 0.014 W, and the output ratio was 95% or more of the output value of the light emitting unit 110. Moreover, in the case where the thickness of the glass part 130 is 5 mm, the output value is slightly increased compared to 0.014 W, and the output ratio of this to the output value of the light emitting unit 110 reached almost 100%.

Furthermore, in the case where the thickness of the glass part 130 is 6 mm, the output value of the rain sensor according to Embodiment 1 was measured as being 0.012 W, and the output ratio of this to the output value of the light emitting unit 110 was 85% or more.

Embodiment 2

In Embodiment 2 of the present disclosure, there is provided a multifocal rain sensor 100 including a light emitting unit 110 which emits light, a first reflective plate 120 which reflects light emitted from the light emitting unit 110, a glass part 130, a parallel unit 160 which is attached to the glass part 130, a second reflective plate 140 which is configured with a multifocal stepped mirror, and a light receiving unit 150.

As a result of measuring the output of light collected into the light receiving unit 150 through the rain sensor according to Embodiment 2, in the case where the thickness of the glass part 130 is 4 mm, the output value was 0.014 W or more, and the output ratio of this to the output value of the light emitting unit 110 was 90% or more. Moreover, in the case where the thickness of the glass part 130 is 5 mm, the output value was 0.015 W which is slightly increased compared to the case of the glass part 130 having a thickness of 4 mm, and the output ratio of this to the output value of the light emitting unit 110 reached almost 100%.

Furthermore, in the case where the thickness of the glass part 130 is 6 mm, the output value of the rain sensor according to the present embodiment was measured as being 0.0145 W, and the output ratio of this to the output value of the light emitting unit 110 was 95% or more. That is, in the rain sensor of the present disclosure configured through Embodiment 2, even when the thickness of the glass part 130 varies from 4 mm to 6 mm, the output value remains constant, so that it is determined that more accurate measurement values can be provided.

In the case of the conventional rain sensor, in the comparative example which included an asymmetric reflective mirror for the glass part 130 varying in thickness from 4 mm to 6 mm, the output value was reduced by the maximum 50%, and it was confirmed that the output ratio was also changed by the maximum almost 50%.

Compared to this, as shown in Embodiment 1, in the case where the second reflective plate 140 having a long focus and a large diameter is used, the sensitivities of the output and output ratio were not greatly varied while the thickness of the glass part 130 was changed from 4 mm to 6 mm. As a result, the present disclosure is characterized in that separate design changes depending on the thickness of the glass part 130 are not required.

Also, in the case of the rain sensor including the second reflective plate 140 configured with the step-shaped mirror as Embodiment 2, the sensitivities of the output and output ratio were not greatly varied while the thickness of the glass part 130 was changed from 4 mm to 6 mm. Moreover, it can be confirmed that as the thickness of the glass part 130 is increased from 4 mm to 6 mm, the output value and the output ratio are slightly increased.

Consequently, in the case of the multifocal rain sensor 100 of the present disclosure, changes in structure and setting of the rain sensor depending on the thickness of the glass part 130 are not required.

As is apparent from the above description, a multifocal rain sensor according to the present disclosure has the following effects.

The present disclosure provides a rain sensor having multiple focuses which can be applied to glass parts having different thicknesses. That is, the rain sensor according to the present disclosure can be applied in common to vehicles with glass parts having different thicknesses.

Furthermore, in the present disclosure, light reflected by a glass part is incident on and reflected by the second reflective plate. In this regard, light can be efficiently collected by the second reflective plate having a predetermined curvature with respect to the vertical direction.

In addition, because the amount of light received into the light receiving unit can be increased by the second reflective plate configured to improve the light collection efficiency, the measurement accuracy of the rain sensor can be markedly enhanced.

The disclosure has been described in detail with reference to embodiments thereof. However, it will be appreciated by those skilled in the art that changes may be made in these embodiments without departing from the principles and spirit of the disclosure, the scope of which is defined in the appended claims and their equivalents.

What is claimed is:

1. A multifocal rain sensor comprising:
   at least one light emitting unit configured to output light;
   a first reflective plate corresponding to the at least one light emitting unit and disposed at a position spaced apart from the at least one light emitting unit by a predetermined distance;
   a glass part reflecting light after the light is reflected by the first reflective plate and forming a sensing region;
   a second reflective plate re-reflecting the light reflected by the glass part; and
   a light receiving unit configured to receive the light reflected by the second reflective plate,
   wherein the second reflective plate includes a multifocal reflective plate having a plurality of focuses based on a vertical height of incident light that varies according to a change in thickness of the glass part.

2. The multifocal rain sensor of claim 1, wherein the second reflective plate includes steps having a stepped shape, and the steps of the second reflective plate having the stepped shape are configured such that reflected light having different phases according to the thickness of the glass part is received by the light receiving unit.

3. The multifocal rain sensor of claim 1, wherein the second reflective plate includes a multifocal parabolic reflective plate.

4. The multifocal rain sensor of claim 1, wherein a focus of the second reflective plate is larger than a focus of the first reflective plate.

5. The multifocal rain sensor of claim 1, wherein the plurality of focuses of the second reflective plate are determined by: $x^2 = 4 \times f \times y$, where x denotes a distance between the second reflective plate and the light receiving unit, y denotes a height of the second reflective plate, and f denotes a focal distance of the second reflective plate.

6. The multifocal rain sensor of claim 1, wherein the second reflective plate includes a parabolic reflective plate having a predetermined curvature with respect to a vertical direction causing different focuses, and having a spherical shape with respect to a horizontal direction.

7. The multifocal rain sensor of claim 1, wherein the at least one light emitting unit comprises an infrared light-emitting diode (LED).

8. The multifocal rain sensor of claim 1, wherein the thickness of the glass part ranges from approximately 4 mm to approximately 6 mm.

9. The multifocal rain sensor of claim 1, further comprising:

a parallel unit disposed on an inner surface of the glass part, wherein the parallel unit makes light reflected by at least one of the first reflective plate and the second reflective plate form parallel light.

10. The multifocal rain sensor of claim 9, wherein the parallel unit includes a serrated lens.

11. The multifocal rain sensor of claim 9, wherein the parallel unit is provided on the sensing region of the glass part and configured to have a bilateral symmetry structure.

12. The multifocal rain sensor of claim 1, wherein the at least one light emitting unit includes two or more light emitting units configured to control light to be received by the light receiving unit through time separation.

13. A vehicle comprising:

a multifocal rain sensor; and a control unit having a memory to store program instructions and a processor to execute the stored program instructions and configured to control an operation of one or more wipers equipped in the vehicle according to information sensed by the multifocal rain sensor, wherein the multifocal rain sensor includes:

at least one light emitting unit configured to output light;

a first reflective plate corresponding to the at least one light emitting unit and disposed at a position spaced apart from the at least one light emitting unit by a predetermined distance;

a glass part reflecting light after the light is reflected by the first reflective plate and forming a sensing region;

a second reflective plate re-reflecting the light reflected by the glass part; and a light receiving unit configured to receive the light reflected by the second reflective plate, wherein the second reflective plate includes a multifocal reflective plate having a plurality of focuses based on a vertical height of incident light that varies according to a change in thickness of the glass part.

* * * * *